United States Patent [19]
Gordon et al.

[11] Patent Number: 5,411,888
[45] Date of Patent: May 2, 1995

[54] IN VITRO TEST FOR DERMAL CORROSIVE PROPERTIES

[75] Inventors: Virginia C. Gordon, Huntington Beach; Soheila Mirhashemi, Laguna Niguel; Rosalind W. Wei, Costa Mesa, all of Calif.

[73] Assignee: Invitro International, Irvine, Calif.

[21] Appl. No.: 98,735

[22] Filed: Jul. 27, 1993

Related U.S. Application Data

[63] Continuation-in-part of Ser. No. 921,023, Jul. 27, 1992, abandoned.

[51] Int. Cl.⁶ .................... G01N 13/00; G01N 21/29
[52] U.S. Cl. ............................................ 436/5; 436/6;
436/8; 436/63; 436/161; 436/164; 436/171;
436/173; 436/530; 422/53; 422/56; 422/58;
422/101; 73/64.47
[58] Field of Search ............. 422/58.61, 70, 89, 82.09,
422/101, 102, 53, 56; 436/6, 8, 63, 161, 171,
173, 5, 164, 530; 514/741, 827, 844; 424/601,
687; 73/64.47

[56] References Cited

U.S. PATENT DOCUMENTS

| | | | |
|---|---|---|---|
| 4,005,191 | 1/1977 | Clark | 424/154 |
| 4,129,647 | 12/1978 | Klein | 424/92 |
| 4,163,800 | 8/1979 | Wickett et al. | 424/326 |
| 4,164,568 | 8/1979 | Bywater | 424/153 |
| 4,593,046 | 6/1986 | Gruber | 514/844 |
| 4,594,884 | 6/1986 | Bondi et al. | 73/64.47 |
| 4,613,574 | 9/1986 | Bergman et al. | 436/2 |
| 4,771,004 | 9/1988 | Higuchi | 436/5 |
| 4,863,696 | 9/1989 | Saydek et al. | 73/64.47 X |
| 4,879,116 | 11/1989 | Fox et al. | 424/682 |
| 5,053,340 | 10/1991 | Bergman et al. | 436/5 |

OTHER PUBLICATIONS

Parish, W. E., "Relevance of in vitro tests to in vivo acute skin inflammation: Potential in vitro applications of skin keratome slices, neutrophils, fibroblasts, mast cells, and macrophages" *Fd. Chem. Toxic* (1985) 23(2):275–285.

Walker et al., "Absorption through human and laboratory animal skins: In vitro comparisons" *Acta Pharm. Suec.* (1983) 20:52–53.

Goldberg, L., Ed., *In Vitro Toxicology: New Directions* (1989) vol. 7, entitled "Alternate Methods in Toxicology" Mary Ann Liebert, Inc., New York, pp. 175–181 and 183–190.

Free et al., "A mathematical contribution to structure–activity studies" *J. Med. Chem.* (1964) 7:395–399.

Goldberg, L., Ed., *Structure-Activity Correlations as a Predictive Tool in Toxicology* (1983) Hemisphere Publishing Corp., New York, A title page and table of contents were previously submitted in the parent application.

Nagao et al., "The effect of sodium hydroxide and hydrochloric acid on human epidermis" *Acta Dermatovener (Stockholm)* (1972) 52:11–23.

Patrick et al., "Mechanisms of chemically induced skin irritation" *Toxicology and Applied Pharmacology* (1985) 81:476–490.

Potokar et al., "Studies on the design of animal tests for the corrosiveness of industrial chemicals" *Fd. Chem. Toxicol.* (1985) 23(6):615–617.

(List continued on next page.)

Primary Examiner—James C. Housel
Assistant Examiner—Harold Y. Pyon
Attorney, Agent, or Firm—Morrison & Foerster

[57] ABSTRACT

Methods for determining the corrosivity of a substance to human skin or membrane are disclosed. In one approach, corrosivity is evaluated by measuring the time required for the test substance to transit a biobarrier that mimics human skin or membranes or the time required to cause a component of such biobarrier to break down and transit the membrane. The invention also envisions alternative approaches which involve series of layers of dyes and corrosive-resistant materials coated onto microspheres or test strips. Use of these methods provides a rapid determination of the corrosivity of test materials.

6 Claims, 7 Drawing Sheets

OTHER PUBLICATIONS

Harvey et al., "The treatment of *Lupus Erythematosus* with mepacrine (atabrine)" *J. Invest. Dermatol.* (1953) 21:99–104.

Harrold et al., "Denaturation of epidermal keratin by surface active agents" *J. Invest. Dermatol.* (1959) 32:581–588.

Choman, B. R., "Determination of the response of skin to chemical agents by an in vitro procedure" *J. Invest. Derm.* (1971) 40:177–182.

Imokawa et al., "Study on skin roughness caused by surfactants: I. A new method in vitro for evaluation of skin roughness" *J. Am. Oil Chem. Soc.* (1975) 512:479–483.

Oliver et al., "An in vitro model for identifying skin-corrosive chemicals: I. Initial validation" *Toxic. In Vitro* (1988) 2(1):7–17.

Imokawa et al., "Study on skin roughness caused by surfactants: II. Correlation between protein denaturation and skin roughness" *J. Amer. Oil Chem Soc.* (1975) 52:484–489.

Imokawa et al., "Cumulative effect of surfactants on cutaneous horny layers: adsorption onto human keratin layers in vivo" *Contact Dermatitis* (1979) 5:357–366.

IN VITRO TEST FOR DERMAL CORROSIVE PROPERTIES

CROSS-REFERENCE TO RELATED APPLICATIONS

This application is a continuation-in-part of U.S. patent application Ser. No. 921,023, filed Jul. 27, 1992, now abandoned.

TECHNICAL FIELD

This invention relates to the field of testing materials for their ability to be corrosive to human skin. More specifically, the invention relates to a device and a method for an in vitro test which can predict the ability of a material to cause corrosion when placed in contact with the human skin.

BACKGROUND ART

As the potential for wider varieties of materials to cause cutaneous damage has become recognized, an increasing effort has been made by industry and environment protection groups to characterize this potential. Federal legislative agencies and commercial manufacturers must consider these risks when developing registering, certifying and shipping materials which could produce toxic effects.

Acute primary irritation is defined as localized reversible inflammatory response of normal living skin to direct injury and is caused by a single application of a chemical agent. Important manifestations are erythema (redness) and edema (swelling). Draize et al., *J. Pharmacol. Exp. Ther.* 82:337, 1944.

Cumulative irritation is also reversible and consists of primary irritation resulting from repeated exposure of skin to materials that do not cause primary irritation, as reviewed by Guillot et al., *Fd. Chem. Toxic* 20: 563, 1982.

Corrosion is defined as direct chemical action on normal living skin that results in its disintegration and irreversible alteration on site of chemical contact. According to Draize et al. (ibid.), it is manifested by ulceration or necrosis.

Animals have been used to test for toxic effects. However, the problems inherent in animal testing contribute to variability of all these methods.

1. Intra-laboratory variability in scoring and handling
2. Individual responses vary considerably
3. Application and occlusive seal
4. Sex and age of animals To evaluate dermal corrosivity, a procedure based on the Department of Transportation Method of Testing Corrosion to skin has been widely used. Code of Federal Regulations, Transportation Title 49, Part 173, Appendix A. Method of Testing Corrosion to the Skin (1983). Six white New Zealand rabbits are shaved, the test substance and a negative control is applied to the shaved skin of each rabbit. Each substances is held in place with a 1×1" square 12-ply surgical gauze pad. Corrosion is found if the test sample caused destruction or irreversible alteration of the tissue on at least two of the six rabbits.

In 1977 the United Nations issued special recommendations for class 8 chemicals. (Transportation of Dangerous Goods. Orange Book. Special Recommendations Relating to Class 8, p. 173.) The distinctions between chemicals in Packing Groups I, II and III were given as follows:

Group 1. Substances that cause visible destruction or irreversible alterations of the skin tissue at the site of contact when tested on the intact skin of an animal for a period of not more than three minutes.

Group 2. Substances, other than those in Packing Group 1, that cause visible destruction or irreversible alterations of the skin tissue at the site of contact when tested on the intact skin of an animal for a period of not more than 60 minutes.

Group 3. Substances, other than those meeting Packing Group 1 or 2 criteria, that cause visible destruction or irreversible alterations of the skin tissue at the site of contact when tested on the intact skin of an animal for a period of not more than four hours.

In recent years, different guidelines have evolved in Europe through legislative activity to classify and label potentially dangerous preparations. 1973 *Off. J. Eur. Comm.* 16 (L189); 1977 *Off. J. Eur. Comm.* 29 (L303); 1978 *Off. J. Eur. Commission* 21 (L296). Different levels of skin corrosion define different classifications of the European Commission (EEC, 1983). Sect 4, No. 404 OECD Paris. A substance is corrosive if, when applied to intact animal skin, it produces full-thickness destruction of skin tissue in at least two animals in four hours. If full-thickness destruction occurs within three minutes, the substance is in R35 class, which is comparable to Packing Group I. If full-thickness destruction occurs between three minutes and four hours, the substance is classified as R34, which is comparable to Packing Groups II and III.

In Vitro Alternatives

The state of development of alternative models for dermal irritation and corrosion is improving rapidly. Attempts have been made to utilize other animals but these have not been well received. Attempts to develop true in vitro alternatives have been centered on three approaches. The first alternative uses patches of excised animal skin maintained in a glass diffusion cell (Parish, *Fd. Chem. Toxic.* 23:278, 1985; and Walker et al., *Acta Pharm. Suec.* 20:52, 1983). The second approach is to use cultured cells and to measure cytotoxicity. (Lamont et al. *In Vitro Toxicology: New Directions*, Vol. 7, Goldberg (ed.), Mary Ann Liebert, Inc., New York City; Naughton et al. *In vitro Toxicology: New Directions*, Vol. 7, Goldberg (ed.), Mary Ann Liebert, Inc., New York City).

The third approach uses mathematical SAR models (Free and Wilson, *J. Med. Chem.* 7:395, 1964; and Goldberg, L., *Structure Activity Correlations as a Predictive Tool in Toxicology*, Hemisphere Publishing Corp., New York, 1983) or physical parameters for prediction effects (Nago et al., *Acta Derm. Venereal Stock* 52:11, 1972; and Patrick et al., *Tox. and Appl. Pharmacol.* 81:476, 1985). One physical parameter frequently described as predictive of corrosivity is pH (Potokar et al., *Fd. Chem. Toxicol.* 23(6):615, 1985). The analysis of pH and acid/alkali reserve was proposed for classification of preparations as corrosive irritant or not classified as dangerous. High or low pH suggests a test sample will be irritant or corrosive but not how irritating. OECD (1981) recognized that test samples with $pH<2$ or $pH>11.5$ are so predictably corrosive that they need not be tested for dermal irritation. However, this basis has incorrectly classified and underestimated corrosive potential and appears to provide only broad guidelines.

It only is applicable to test materials which can be called acid or alkali.

All of the foregoing methods for predicting skin corrosion have limitations. The in vitro methods require living cells or isolated tissues or are very limited to specific chemicals such as in SAR. While these procedures do provide an alternative to animal testing, they do not achieve the simplicity and standardization one experiences with other standardized tests. The method of the present invention offers such a test. It provides a standard, quick, reproducible, objective measure of the capacity of materials to cause corrosion.

Scientists have utilized dermal biomacromolecules to study potential effects of chemical and formulations on the skin for the last forty years. As early as 1953, Scott and Lyon quantified an increase in exposed sulfhydryl groups of keratin after soaps and detergents were applied to the keratin. This exposure resulted from a separation of keratin chains (Van Scott and Lyon, *J. Invest. Dermatol.* 21:99, 1953). A relationship between the degree of denaturation or separation, the effects of different soaps and detergents on keratin, and the incidence of in vivo dermatitis due to these compounds was observed. Harrold (1959) expanded this work to include investigation of complete formulations on keratin denaturation and separation (*J. Invest. Dermatol.* 32:581). In 1971, Choman evaluated the swelling response of in vitro skin discs prepared from dermal calf collagen (*J. Invest. Derm.* 40:177). Sodium lauryl sulfate produced a swelling response, and similar responses for a series of anionic and nonionic surfactants were directly related to their skin irritation potential. Further research clearly established swelling of isolated epidermis and synthetic dermal membranes as a parameter related to irritation. Such swelling is based on adsorption onto and disruption of the three-dimensional keratin protein matrix. Adsorption of the stratum corneum was thoroughly investigated by Imokawa et al., who established a correlation between skin roughness in vivo and in vitro (*J. Am. Oil Chem. Soc.* 52:475). This and other studies established adsorption as a major step in the initiation of dermal irritation and as perhaps the most important physicochemical parameter in the dermal toxicity of anionic surfactants.

A second major parameter in the initiation of irritation, integrity of the stratum corneum, has been investigated recently. Pemberton and Oliver used monitoring of electrical resistance in skin slices as a measurement of barrier integrity and as an indicator of the corrosive potential of chemicals (*Toxic. In Vitro* 2:7, 1988). They showed that corrosive agents have a greater ability than noncorrosives to exert a direct physicochemical lytic action on the stratum corneum. Many chemical toxicants produce changes in the keratin barrier matrix in direct proportion to their adsorption to and interaction with the barrier as studies by Van Scott, Harold, Choman and Imokawa (supra). These changes correlate with their potential to produce dermal irritation and corrosion.

DISCLOSURE OF THE INVENTION

One embodiment of the invention provides a method for determining the degree of corrosive toxicity of a test substance to human skin or membrane. This method includes first applying the test substance at a first time to a first face of a biobarrier which also has a second face. This biobarrier mimics human skin or membrane to be tested. The biobarrier has its a second face in contact with a chemical detection system which includes at least one indicator. The method secondly includes allowing the test substance to transit to the biobarrier's second face and contact the chemical detection system. The method thirdly includes detecting the test substance in the chemical detection system at a second time. The method fourthly includes obtaining the difference between the first and second times, with the time difference being roughly inversely proportional to the corrosive toxicity of the test substance. In another aspect of this invention, the chemical detection system is formulated to detect one of the breakdown products that the corrosive substance liberates in transit through the biobarrier. In another aspect of this invention, after the test substance is applied to the biobarrier, sunlight, or ultra-violet light, is applied to the biobarrier; and the amount of protein liberated from the biobarrier is measured by the chemical, or protein, detection system, as well as any other physical, chemical or optical detection system.

In a second embodiment, the invention provides a method to determine the effect of a test substance on the known detection time of a dermal corrosive substance. As a first step, this method provides combining the test substance with a corrosive substance to obtain a mixture. Second, the method provides applying the mixture at a first time to a first face of a biobarrier having a second face, which biobarrier mimics human skin or membrane to be tested, the second face of the biobarrier contacting a chemical detection system comprising at least one indicator. Third, the method provides allowing the mixture to transit to the biobarrier's second face and contact the chemical detection system. Fourth, the method provides detecting the mixture in the chemical detection system at a second time. Fifth, the method provides obtaining the difference between the first and second times to obtain a detection time for the mixture. And finally the method provides comparing the detection time of the mixture with the known detection time of the known corrosive substance. When the mixture has a longer detection time than the known corrosive substance, then the test substance has an anti-corrosive effect.

There is further provided a method of classifying a test substance as nontoxic or in toxic UN Packing Groups. First, this method provides for applying the substance at a first time to a first face of a biobarrier having a second face. This biobarrier mimics human skin in speed of response to known corrosive substances. The biobarrier also has a second face in contact with a chemical detection system, which includes at least one indicator. Second, the method provides for allowing the test substance to transit the biobarrier to the second face where it contacts the chemical detection system. Third, the method provides for detecting the substance in the chemical detection system at a second time. Fourth, the method provides for obtaining the difference between the first and second times. And fifth, the method provides for correlating this time difference with the times stated in the UN Packing Group designations, and thereby assigning the test substance a designation. In this method, if the time difference is less than 3 minutes, the test substance is assigned to UN Packing Group 1. If the time difference is more than 3 minutes but less than 60 minutes, the substance is assigned to UN Packing Group 2. If the time difference is greater than 60 minutes but not more than four hours, the test substance is assigned to UN Packing Group 3.

Another embodiment of this invention is a device for performing an in vitro test to determine the corrosiveness of a test substance to human skin or membrane. This device has a biobarrier with a first face and a second face. The biobarrier mimics human skin or membrane and has characteristics so as to permit measurement of time for a test substance to traverse therein. This device also has in contact with the second face of the biobarrier a chemical detection system, including at least one indicator, which detects when the test substance has passed through the biobarrier into the chemical detection system. This device further has a means for recording a first time when the test substance is applied to the first face of the biobarrier and for recording a second time when the test substance has traversed the biobarrier and is detected by the chemical detection system. And finally, the device includes a means for reporting the difference between the first and second times.

There is further provided a method of classifying a test substance as nontoxic or in toxic EEC R34 and R35 classes. First, this method provides for applying the substance at a first time to a first face of a biobarrier having a second face. This biobarrier mimics human skin in speed of response to known corrosive substances. The biobarrier also has a second face in contact with a chemical detection system, which includes at least one indicator. Second, the method provides for allowing the test substance to transit the biobarrier to the second face where it contacts the chemical detection system. Third, the method provides for detecting the substance in the chemical detection system at a second time. Fourth, the method provides for obtaining the difference between the first and second times. And fifth, the method provides for correlating this time difference with the times stated in the EEC R34 and R35 classes, and thereby assigning the test substance a designation. In this method, if the time difference is less than 3 minutes, the test substance is assigned to EEC class R35. If the time difference is more than 3 minutes but less than four hours, the test substance is assigned to EEC class R34.

There is further provided a method for determining the degree of corrosive toxicity of a substance to skin. This method involves applying the test substance at a first time to a first face of a biobarrier with a second face. The biobarrier has its second face in contact with an electronic detection system, which comprises an indicator. In this method, the test substance transits the biobarrier to affect an indicator which is electronically detected at a second time. The difference in times is inversely proportional to the corrosive toxicity of the test substance.

In an alternative embodiment, the electronic detection system includes a sensor, or dosimeter. The dosimeter is affected by the test substance or material liberated from the biobarrier by the test substance. The effect on the dosimeter is correlated with the degree of corrosivity.

There is further provided a method for determining the degree of corrosive toxicity of a substance to skin. This method involves applying the test substance at a first time to a first face of a biobarrier with a second face. The biobarrier has its second face in contact with an mechanical detection system. In one embodiment, the mechanical detection system includes at least one indicator. In this method, the test substance transits the biobarrier to affect the indicator. The mechanical detection system detects the change in the indicator at a second time. The difference in times is inversely proportional to the corrosive toxicity of the test substance.

In an alternative embodiment, the mechanical detection system comprises a lever which is in contact with the biobarrier. The lever system shifts in response to contact with the test substance which has transited the biobarrier. The amount of shifting of the lever system is correlated to the degree of corrosivity of the test substance.

There is further provided a method for determining the degree of skin corrosive toxicity of a test substance with a test stick. The test substance is applied to the test stick, which includes a series of interspersed corrosive resistant materials and dyes. The stick's surface is a first layer composed of modestly corrosion-resistant material such that the second layer comprising a first dye immediately underlying the first layer is exposed by virtually all corrosive substances. The third layer underlies the second layer and is a more corrosion-resistant material than the first layer. The fourth layer is a second dye immediately under the third layer and is exposed by highly corrosive substances. The fifth layer underlies the fourth layer and is the most corrosion-resistant material of the three corrosion-resistant layers. Under the fifth layer is the sixth layer which is the third dye which is exposed only by extremely corrosive substances. The test substance contacts the test stick for more than 1 second. Then the color of the test stick is observed.

A further embodiment of a test for determining the degree of corrosive toxicity of a test substance utilizes microspheres. The microspheres comprise layers of increasingly corrosion-resistant materials and interspersed dyes, such the most corrosive substances eat through more layers of the microspheres and expose dyes in or under these layers. The microspheres have a first, surface layer of modestly corrosion-resistant material, such that the second layer with a first dye immediately under the first layer is exposed by virtually all corrosive substances. The third layer underlies the second layer and is a more corrosion-resistant material than the first layer, such that the fourth layer (the second dye) immediately under the third layer is exposed by only highly corrosive substances. The fifth layer is under the fourth layer and is the most corrosion-resistant material of the corrosion-resistant layers, such that the sixth layer (the third dye) is exposed only by extremely corrosive substances. The test calls for applying the test substance to the microspheres, with which the test substance is in contact for more than 1 second, and observing the color of the test microspheres.

In yet another embodiment, there is provided a method for determining corrosivity by means of contact with microspheres. The microspheres are prepared by applying a layer of corrosion-resistant material of one color to an underlying particle of a second color. Corrosive substances will expose the second color. The test involves contact the microspheres with the test substance for more than one second. Then the color of the microspheres is observed to determine if the test substance exposed the second color. In a related embodiment, the particles are coated with two or more different standard thicknesses of corrosion-resistant material and the underlying particles are two or more different colors; this permits gradation of the corrosivity by the number of colors which are exposed.

In another embodiment, the corrosivity of a test substance is measured by applying the test substance to a test stick covered with microspheres. The microspheres have been prepared applying a layer of corrosion-resistant material of one color to an underlying particle of a second color. If the test substance is corrosive, the second color is exposed. The test proceeds with the test substance in contact with the test stick for more than one second. The color of the test stick where the test substance was applied is observed. In a related embodiment, the test stick is coated with microspheres containing particles coated with two or more different standard thicknesses of corrosion-resistant material and the underlying particles are two or more different colors; this permits gradation of the corrosivity by the number of colors which are exposed.

In another embodiment, there is provided a method for determining the penetration of a test substance. In this method, a test substance is applied at a first time to a penetration barrier, which has a first and a second face. This penetration barrier mimics human skin or other membrane to be tested. The second face of the penetration barrier contacts a detection system. The test substance is then allowed to transit the penetration barrier to the second face, where it contacts the detection system. The detection system detects the test substance at a second time to obtain a detection time, which in turn can be correlated with in vivo penetration times.

In another embodiment, there is provided a method for classifying test substance according to the UN Packing groups with a dry chemical indicator. This dry chemical indicator registers a change in response to exposure to a corrosive test substance which varies with the UN Packing Group. The test substance is exposed to the dry chemical indicator, which is then observed for a change. The change is correlated with the UN Packing Group. The change can be in color or in curvature. In another embodiment, the change in the dry chemical indicator can be correlated with the EEC classes of corrosivity.

MODES OF CARRYING OUT THE INVENTION

A. Definitions

Figure 1:
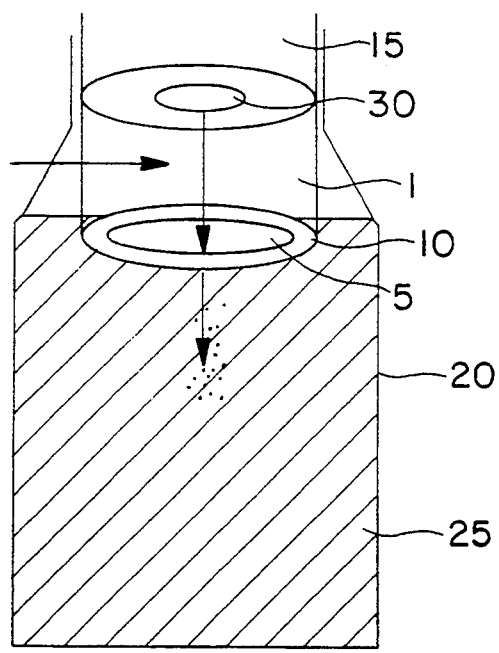
FIG. 1 illustrates in a cutaway view the biobarrier/chemical detection system of this invention.

"Dermal corrosion" is the corrosive toxicity of a substance on the human skin and refers to the ability of the substance to cause alteration or destruction of human skin as measured by ulceration or necrosis. Corrosion is evidenced by cracking, fissures and blisters. Corrosion is a much more severe response than irritation, which is evidenced by erythema and edema.

A "chemical detection system" (CDS) refers to a chemical system that detects a test substance. The chemical detection system can be a liquid or a solid, usually a mixture, which may be clear or colored, and contains an indicator. When a substance is present in the CDS, a change in the CDS indicator occurs. Other chemical detection systems will detect breakdown products of the biobarrier, including protein. Other chemical detection systems contemplated in this invention include high pressure liquid chromatography, gas chromatography, mass spectroscopy, nuclear magnetic resonance and the like.

A "biobarrier" refers to the protein gel matrix to which test samples are applied. The biobarrier has a first face and a second face. The test sample is applied to the first face of the biobarrier, and the substance exits the biobarrier at the second face of the biobarrier. Generally, the biobarrier consists of biomacromolecules found in the skin or biomacromolecules which are structurally related to those found in the skin. The biobarrier includes a base membrane to which is optionally bound at least one protein. The base membrane is composed of non-proteinaceous, film-forming polymer, such as cellulose, nitrocellulose, or other similar material known to those skilled in the art. The protein which may be bound to the base membrane may be cross-linked keratin, cross-linked collagen or mixtures thereof. Alternately, the protein may be a synthetic protein or a plant protein capable of forming a gel network.

A test substance transits the biobarrier generally by breaking chemical bonds in the biobarrier.

Detection time is defined as the difference between a first time at which the test substance is applied to the biobarrier and a second time when the test substance or other material is detected in the chemical detection system. The longer the detection time, the less corrosive is the test substance. The biobarrier can be designed to give corrosion times that approximate those of in vivo tests, or it can be designed to provide a number which must then be corrected to arrive at a corrected detection time. Such an actual or corrected detection time is said to correlate with that of the in vivo test. Substances with short detection are more corrosive than those with longer detection times, while those that correlate with in vivo corrosion times greater than four hours are considered noncorrosive.

An anti-corrosive substance is one which when combined with a known corrosive agent and exposed to the device of the current invention, has a detection time greater than does the known corrosive agent alone.

B. General Description

B.1. General Parameters of the Testing Procedure

One aspect of the present invention provides a method and apparatus for performing an in vitro test for dermal corrosiveness of a test substance. The invention provides a biobarrier and chemical detection system (CDS). The test substance is applied to the biobarrier at a first time. If it is corrosive, the test substance crosses the biobarrier and is detected by the CDS at a second time. The time it takes the test sample to move through and destroy the biobarrier depends in the degree of corrosivity of the test sample. The biobarrier and CDS are designed to produce a response which is detectable at a time which is roughly inversely proportional to the corrosion of the sample to be tested.

The biobarrier has characteristics to permit transit times which correlate with the time of skin response to known corrosive chemicals. The biobarrier is formed from a standardized mixture of materials which has the advantages and properties of standardized in vitro tests using chemical reagents. The biobarrier can be prepared in dishes, wells, discs, trays, etc.

In another aspect, the biobarrier is composed of a base membrane and any of a variety of macromolecular networks such as keratin, collagen, keratin/collagen mixtures and synthetic or plant proteins capable of forming gel networks.

When the test substance destroys the biobarrier, the test substance enters the CDS where it is detected, for example, by the formation of color and/or precipitate in the CDS. Color or precipitate formation can be assessed using a variety of techniques that are described in detail below.

For example, in one embodiment, the invention provides a solution of chemical indicators which recognizes 14 classes of chemicals, such as oxidizing chemicals, reducing chemicals, alkali and acid. When the test substance interacts with the CDS, a visible or measurable change can be observed or read spectrophotometrically.

In another aspect, the invention is directed to a method wherein the CDS provides a protein indicator to detect the release of destroyed or degraded protein as an endpoint of corrosivity.

In another aspect, the invention is directed to a screening method to predict corrosivity of a test sample where the test sample is applied to the biobarrier and its release can be detected by high pressure liquid chromatography (HPLC), gas chromatography (GC), ultraviolet (UV), and visible light spectrum (VIS) as well as any other physical, chemical, optical, mechanical or electronic detection system. If the chemical is released quickly, it is corrosive. If the chemical takes longer and correlates with in vivo corrosion times greater than four hours, it is noncorrosive.

In another variation, a more sophisticated chemical detection system could use HPLC, GC, mass spectroscopy or NMR to detect the test substance or a biobarrier breakdown product which is released at a particular time. The automated electronic or mechanical equipment can be set up to scan the CDS at intervals and record the change, for example, on a strip chart. Then the detection time could be determined.

In another embodiment, the biobarrier/CDS can identify whether a complex mixture has at least one component which is corrosive. Then, identification of the corrosive component can be made chemically. If substances from a complex mixture transit the biobarrier at different times, they can be collected and analyzed. A biobarrier/CDS testing the corrosivity of 1–20 components is contemplated. Standard absorbance readings are made to detect the substance entering the CDS.

In another aspect of the invention, the degree of corrosivity, determined by the test substance's detection time, can be correlated with the UN Packing Group Assignments. If the actual or corrected detection time is not more than three minutes, the test substance is classified as Group 1. If the detection time exceeds three minutes but is less than 60 minutes, the test substance is classified as Group 2. If the detection time exceeds 60 minutes but is not more than four hours, the test substance is classified as Group 3. The test substance is classified as noncorrosive if the CDS detects no test substance in four hours. The inventive method can also be used as a noncorrosive/corrosive screen.

In another embodiment, the method quantifies the protein released from the biobarrier. The first detection of protein release from the biobarrier using optics, protein reagents, or fluorescence as an indication of the degree of corrosivity of the test substance.

In still another embodiment, the method of the invention can also be used to identify and quantitate the anticorrosivity of a test substance. Anticorrosives protect a tissue, organ, or molecule from the corrosive effects of a known corrosive substance. First, the biobarrier of the system is pretreated with an unknown potentially anticorrosive substance. Then a known corrosive chemical can be applied to the biobarrier, and the detection time is quantified. Then, the detection time for the corrosive chemical alone is compared to the detection time for the test substance and the corrosive chemical. If the detection time for the test substance is greater than that for the corrosive chemical alone, then the test substance is anticorrosive. The difference in detection times indicates the degree of anticorrosivity.

In another aspect, the anticorrosivity of a substance can also be determined by premixing a sample containing a potential anticorrosive and a known corrosive and then applying the resulting mixture to the system. An increase in the detection time produced by the corrosive and anticorrosive with respect to the detection time produced by the corrosive alone is again indicative of the anticorrosivity potential of the anticorrosive. The optimal combination of the anticorrosive and the corrosive can be determined by varying the ratios of the substances.

B.2. The Biobarrier

As shown in FIG. 1, the biobarrier 1 is formed from a colored or uncolored pliable network of macromolecules. The biobarrier is chosen to mimic the particular skin or membrane that would be corroded. In assembly, a base membrane 5, which is a semipermeable membrane, is placed between two concentric rings 10 in the bottom of an individual well 15. The biobarrier 1 is placed on or poured onto the base membrane 5. In vial 20, under well 15, the chemical detection system (CDS) 25 is placed so that the CDS 25 is in contact with base membrane 5. In use, the test substance 30 is applied onto the top or first face of biobarrier 1, and the time is noted. If test substance 30 is corrosive, it destroys biobarrier 1 and passes through the biobarrier 1 to the second face of the biobarrier and base membrane 5 into the CDS 25. This change in CDS 25 is either visually observed or recorded by a machine, and a second time is noted. The difference in the two times is roughly inversely proportional to the corrosiveness of the test substance 30.

The biobarrier 1 itself is a combination of a semipermeable base membrane 5 and cross-linked protein. The semipermeable base membrane 5 is composed of nonproteinaceous, film-forming polymer, such as cellulose or nitrocellulose. The protein bound to the membrane is preferably keratin and/or collagen or a combination thereof. The protein is preferably crosslinked. The biobarrier can be made from keratin or collagen by using salt solutions as a diluent as well as glycols. Salt solutions include water solutions with 0% up to about 1.5% salts. Preferably, about 0.9% saline (sodium chloride) solution is used. Salts can be varied and can include but are not limited to magnesium chloride, potassium chloride, sodium bicarbonate and combinations thereof. Optionally, ethanol and other polar diluents can be used with, or instead of, water. Examples of glycols include but are not limited to ethylene, propylene, hexylene and polypropylene glycol and mixtures thereof. Optionally, a bifunctional crosslinking reagent such as dimethylsuberimidate may be used to crosslink the proteins to the cellulose or nitrocellulose membrane. The resulting biobarrier mimics the stratum corneum barrier of the skin. Optionally, enzymes can be added to represent different tissues.

According to the present invention, the biobarrier 1 can also be constructed so as to mimic mucous membrane such as the buccal, vaginal, or penile membrane. In such a form, no keratin or collagen is added to the biobarrier 1. Other skin types that can be mimicked with this system include, but are not limited to, chapped hands, callouses, bunions, plantar's warts, eczema, sun burn and skin rashes of various types.

According to the present invention, the diluent components can be varied to produce biobarriers representing the skin of different animal species, different locations on the animal's body and different ages of the animals. For example, when a higher percentage of diluent is used, there is less protein on the matrix, mimicking the body's more sensitive (less exposed to the elements) skin and younger skin. For example, in older skin, there is less water and lipid, and that can also be mimicked by adjusting biobarrier ingredients. Also, the ingredients used to make the biobarrier can be adjusted so that the biobarrier mimics facial skin, or other areas of the body, as indicated for cosmetic, emollient or medication applications. With a higher level of glycol(s), the biobarrier is harder, mimicking older skin.

In addition to the above-described synthetic biobarriers 1, animal membranes and/or skin such as snake or pig skin can be used for the biobarrier 1. In this case, it is not necessary to crosslink the keratin protein present because it is already extensively crosslinked naturally.

A lipid component can also be added to a keratin/collagen crosslinked synthetic biobarrier 1 by covalently attaching, coupling, and/or binding fatty acid or cholesterol or acylceramide to the crosslinked biobarrier 1. The amount and kind of lipid in human skin varies widely depending on body location, diet, ethnicity, and other parameters. A lipid component changes the permeability characteristics of the biobarrier 1. Therefore, any lipid should only be added to the basic synthetic membrane when its importance in the skin has been evaluated.

Other components such as preservatives (for example, formaldehyde) or stabilizers (for example crosslinking agents) may be added to the biobarrier. These components may affect the time and other biobarrier characteristics may need to be adjusted to accommodate these chemicals.

The biobarrier height can also be adjusted for various conditions and embodiments. For example, the biobarrier height can be calibrated so that UN Packing Group 3 corrosive substances corrode the biobarrier in the same time period as rabbit skin is eroded (60 minutes to 4 hours). Alternately, the biobarrier height can be varied so that the test can run in different time periods, either more quickly for faster assessment or more slowly for convenient assessment after overnight incubation. Then the detection time is corrected by multiplying by a correction factor, and the corrected time is compared with known times.

When a test substance 30 is evaluated for dermal corrosion by the method of the invention, the substance is applied to the first face of biobarrier 1, and the time is noted. Then, corrosive substance 30 destroys the biobarrier 1 and causes release of portions of the substance 30 and/or protein and/or other components from the biobarrier 1 into the CDS 25. When substance 30 or another material is detected in the CDS 25, a second time is noted. The difference between the first and second times is the detection time. The greater the corrosion of the biobarrier 1, the faster the release of the test substance 30 into the CDS 25, and the smaller is the detection time.

B.3. The Chemical Detection System (CDS)

In this embodiment, the CDS is provided in the form of a clear aqueous liquid with at least an indicator which detects the presence of the test substance. The CDS is exposed to the test substance after the substance has been placed on the biobarrier and penetrates the permeable membrane.

The indicator is composed of active ingredients which change color or precipitate. Color-changing indicators include, but are not limited to, cresol red and methyl orange. For precipitation, the active ingredients of the CDS are solutes of colloidal particles which remain in solution until the substance penetrates the biobarrier and enters the solution and produces precipitation. The CDS can contain a number of different chemical indicators, which are well known to those skilled in the art.

To maintain a compatible pH range and ionic strength, the CDS is provided with ions and buffers which are used to adjust the buffering capacity and ionic strength of the precipitants and/or indicators used. Suitable compounds include but are not limited to phosphate salts, acetate salts, Tris-Cl, borate, and a variety of other compounds known in the art. Preferably, ionic strength can vary over a wide range of about 0.005M to 0.05M.

B.4. Electronic Detection System

Figure 2:
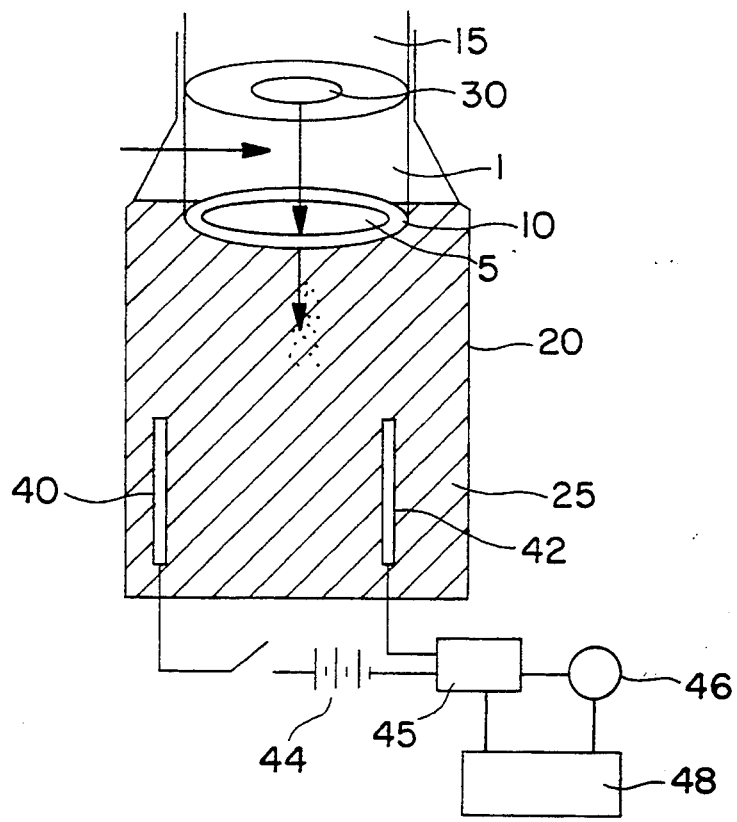
FIG. 2 illustrates a chemical detection system modified to include electronic detection with a pair of electrodes and display of the test results.

The CDS detection system described above may be modified to include electronic detection and display of the test results. For example, a pair of electrodes 40 and 42 may be placed in the CDS 25 in vial 20, as shown schematically in FIG. 2. A small voltage is applied across electrodes 40 and 42 by a voltage source 44 such as a battery or a transformer. The magnitude of the applied voltage is selected so that no current flows between the electrodes through the CDS in the initial composition of the CDS (i.e., prior to any reaction with the test substance).

The CDS is chosen so that when a quantity of test substance 30 and/or a portion of the biobarrier 1 enters the CDS, a chemical reaction occurs to increase the ion concentrations in the CDS. This increase in ion concentration increases the conductivity of the CDS, thereby permitting current to flow between electrodes 40 and 42, as measured by ammeter 45. A timer 46 determines and displays the detection time, that is, the time between when the test substance first contacts the biobarrier and the time when a current is first detected by ammeter 45. A separate display 48 such as a CRT or a strip chart may also be provided to show plots of current versus time and/or digital representations of current and time information along with current change rate information. An alternative embodiment includes a dosimeter, or sensor capable of sensing, for example, sodium hydroxide or potassium hydroxide, which are released from the biobarrier. When signals from the dosimeter increase, the biobarrier has been breached by corrosive substance. The timing of the signals or rate of signals can be correlated with the corrosivity of the test substance.

Figure 3:
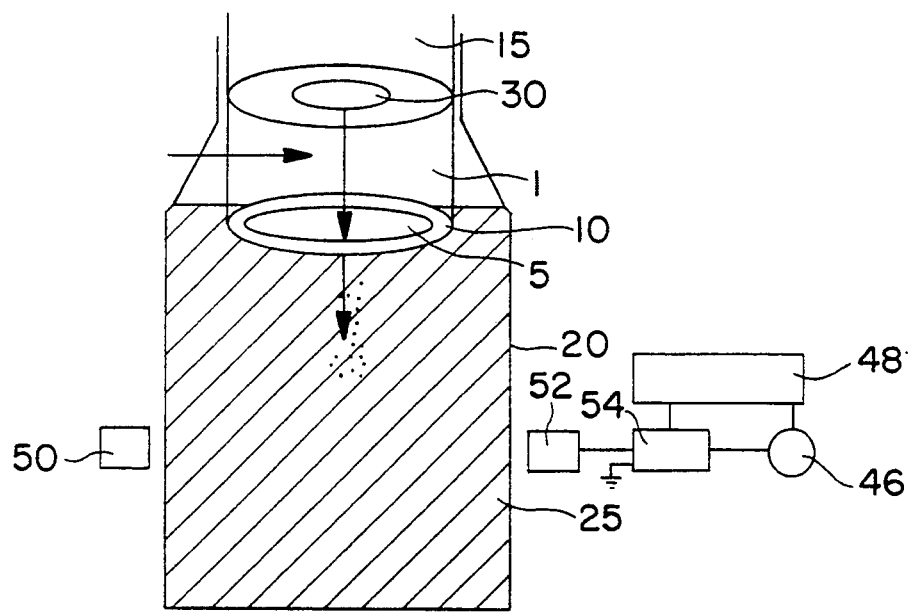
FIG. 3 illustrates modification of the chemical detection system to incorporate spectrophotometric observation of color change.

Another modification of the CDS is shown schematically in FIG. 3. In this embodiment, a color change in the CDS (as described above) is used to detect the penetration of biobarrier 1 by the test substance. Instead of visual detection of the color change, however, an electronic color detection system is used. Specifically, a light source 50 and photodetector 52 are disposed on opposite sides of transparent portions of vial 20. The amount of light transmitted through the CDS in the vial diminishes as the CDS color changes from transparent to the color of the selected pH indicator dye (e.g., blue or violet). As the amount of light received by photodetector 52 diminishes, the voltage generated by photodetector 52 decreases, as measured by voltmeter 54. Once again, this embodiment has a timer 46 and a display 48 to provide information on detection time, or elapsed time between initial contact of the test substance with the biobarrier and the later contact of the test substance with the CDS. This embodiment also can be adjusted to provide the rate of change of the CDS color.

Figure 4:
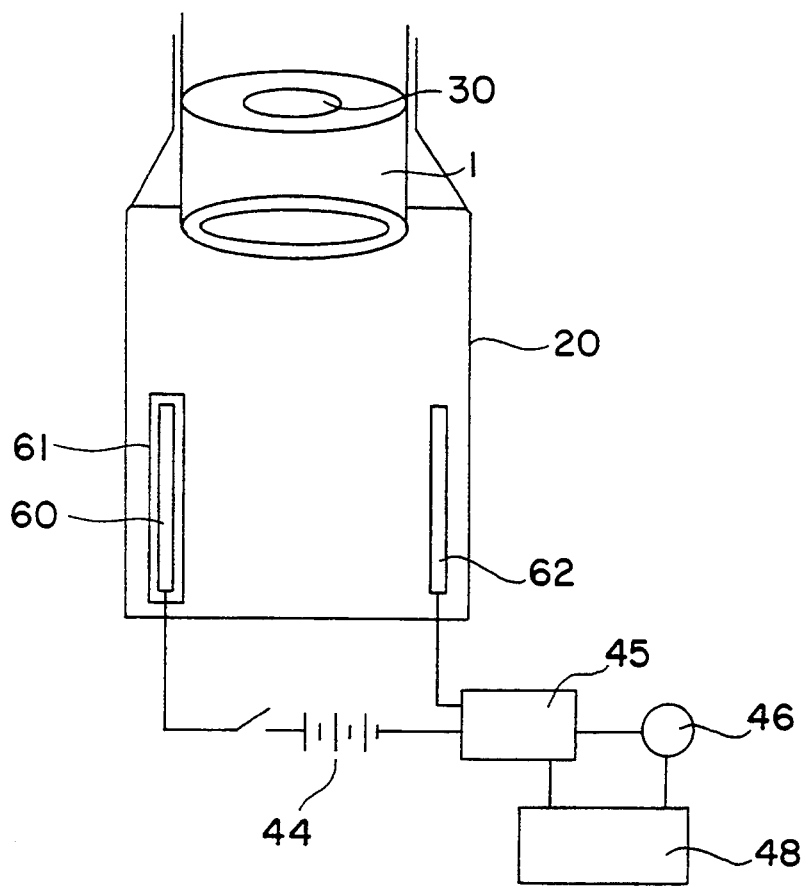
FIG. 4 illustrates modification of the chemical detector to incorporate an electrode with a chemically reactive coating which is eroded by passage of corrosive substance through the biobarrier.

FIG. 4 shows yet another alternative to the CDS detector described above. In this embodiment, vial 20 contains an electrically conductive solution such as saline. Electrodes 60 and 62 are disposed in the CDS solution, as before. In place of the chemically reactive portions of the CDS, however, is a chemically reactive coating 61 on one of the electrodes, such as a substance that will enzymatically produce ions for charge transfer from the saline to the electrode when contacted by the test substance. A timer 46 and display 48 are provided, as in the other embodiments.

Figure 5:
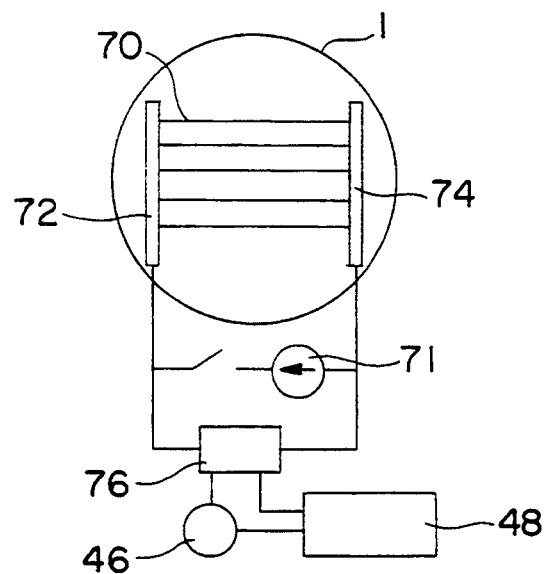
FIG. 5 illustrates a network of conductive traces in the biobarrier which is broken by a corrosive test substance, to reduce current and trigger a detection time.

FIG. 5 shows an embodiment that does not rely on the chemical interaction of the test substance with a CDS. The biobarrier 1 of this embodiment has a network of conductive traces 70 formed on the back surface of the biobarrier 1 and electrically interconnected to junctions 72 formed on opposite sides of the membrane. During the test, a current source 71 applies current from junction 72 and to junction 74. A voltmeter 76 measures the voltage drop between the junctions. As the test substance corrodes the biobarrier, one or more conductive traces will be broken, thereby raising the electrical resistance measured between junctions 72 and 74. A timer 46 and display 48 may be used to measure and display the elapsed time for the corrosive activity and the relationship between time and voltage rise.

B.5. Mechanical Detection System

Figure 6A:
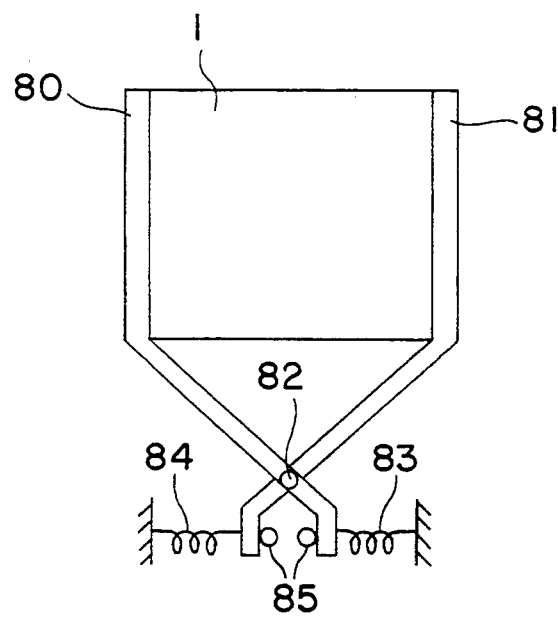
FIGS. 6a and 6b illustrates a mechanical detection system in which corrosion triggers movement which breaks an optical connection.
Figure 6B:
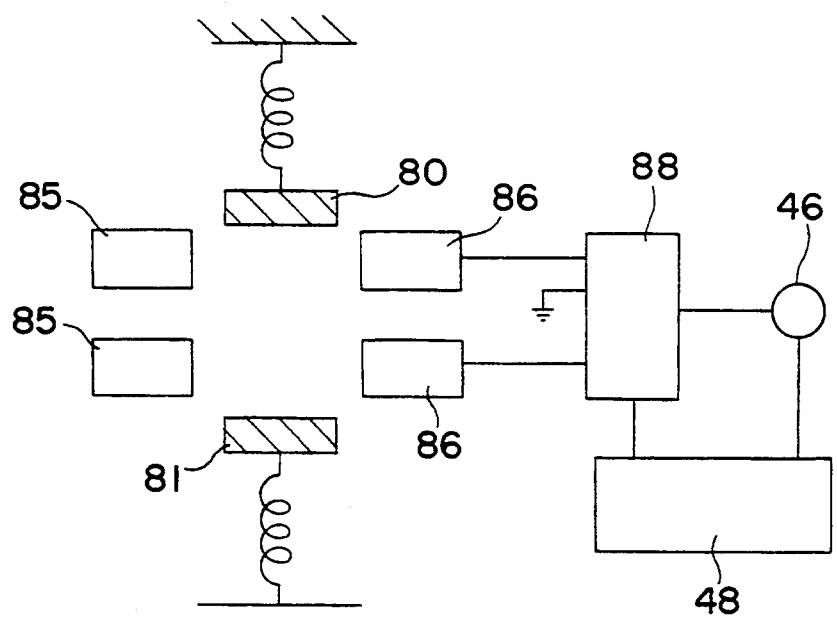

FIGS. 6(a) and 6(b) show a mechanical detection embodiment of this invention. In this embodiment, biobarrier 1 is suspended between two gripping arms 80 and 81. Arms 80 and 81 are connected at a pivot point 82, and a pair of springs 83 and 84 are disposed to move the arms apart in order to provide tension across biobarrier 1. A motion detector such as light sources 85 and photodetectors 86 are placed to detect movement of either arm. In use, corrosion of the biobarrier by the test substance causes the biobarrier to weaken and stretch, thereby permitting arms 80 and 81 to move apart. Movement of either arm breaks the optical connection between a light source 85 and its respective photodetector 86, thereby sending a signal to system timer 46 via a logic unit 88. Detection time may be read from display 48.

Figure 7:
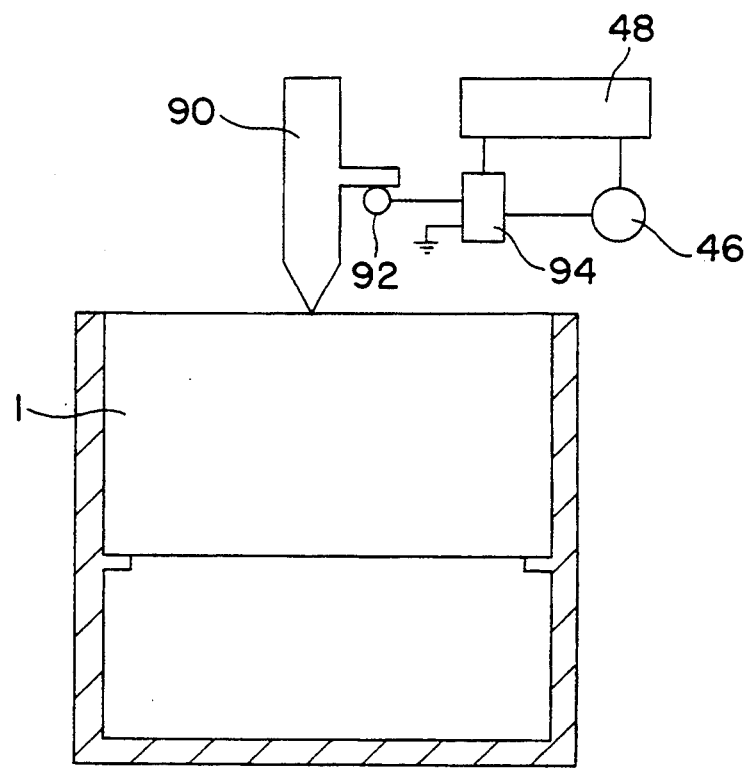
FIG. 7 illustrates another mechanical embodiment.

FIG. 7 shows another mechanical embodiment of this invention. In this embodiment, a single arm 90 provides downward tension on biobarrier 1. A light source/photodetector arrangement detects motion by arm 90 (only the photodetector 92 is shown in the drawing). In use, corrosion of the biobarrier by the test substance will cause the biobarrier to weaken and stretch, thereby permitting arm 90 to move downward toward the biobarrier. This motion breaks the optical connection between the light source and the photodetector (as detected by logic unit 94) to stop the elapsed time clock 46. Detection time, or elapsed time, may be displayed on display 48.

In another embodiment of the mechanical detection system, one arm of a lever system is in contact with the lower surface of the biobarrier. This arm of the lever shifts in response to contact with the test substance which has transited the biobarrier. The amount of shifting of the lever system can be correlated with the degree of corrosivity.

B.6. Test Microspheres

Figure 8:
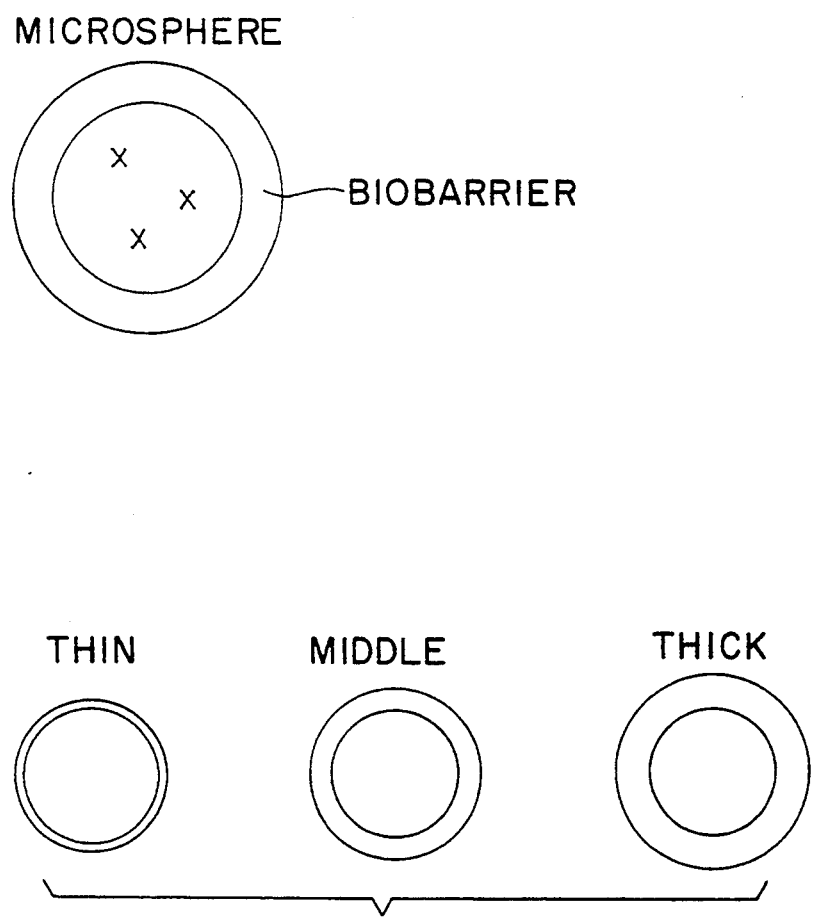
FIG. 8 illustrates test microspheres having three different thicknesses of a corrosion-resistant material overlying three different colored particles.

In another embodiment, shown in FIG. 8, there are provided test microspheres. The test microspheres are composed of an outer, corrosion-resistant biobarrier of one color which coats an underlying particle of another color. The biobarrier has a standard thickness for reproducibility and correlation with other corrosion test methods. When the microspheres are in contact with a corrosive test substance for at least one second, the underlying color is exposed and is detectable. This color change is not dependent on the corrosive substance reacting to produce a color change. Therefore, this method is considered more universally applicable.

In another embodiment, the microspheres are prepared with multiple standard thicknesses of the biobarrier. The underlying particle has different colors depending on the overlying biobarrier thickness. The microspheres are exposed to the test substance for a standard period of time, at least one second. Non-corrosive substances will not erode the biobarrier, so only the biobarrier color will be visible. Somewhat corrosive substances will only erode the thinnest layer of the biobarrier, revealing only one underlying color. Increasingly corrosive substances erode the thicker biobarrier layers, revealing two or more underlying colors. Thus, the degree of corrosivity can be determined and correlated with other corrosivity tests. Optionally, the test substance is removed (for example, rinsed off) after a standard time period and before observing for color. In lieu of visible colors, fluorescent dyes can be incorporated into the outer or underlying layers of the microspheres. Increases or decreases in fluorescence can be correlated with corrosivity. Alternately, the microspheres can be designed so that a gas is liberated as the surface of the microspheres is eroded by corrosive substances, and the rate of gas formation can be correlated with corrosivity. In yet another embodiment, the outer layer of the microspheres comprises magnetically attractive materials. As the outer layer is corroded, fewer of the microspheres are magnetically attracted; the proportion of microspheres magnetically attracted after a standard interval can be inversely correlated with corrosivity.

B.7. Test Dipstick

Figure 9:
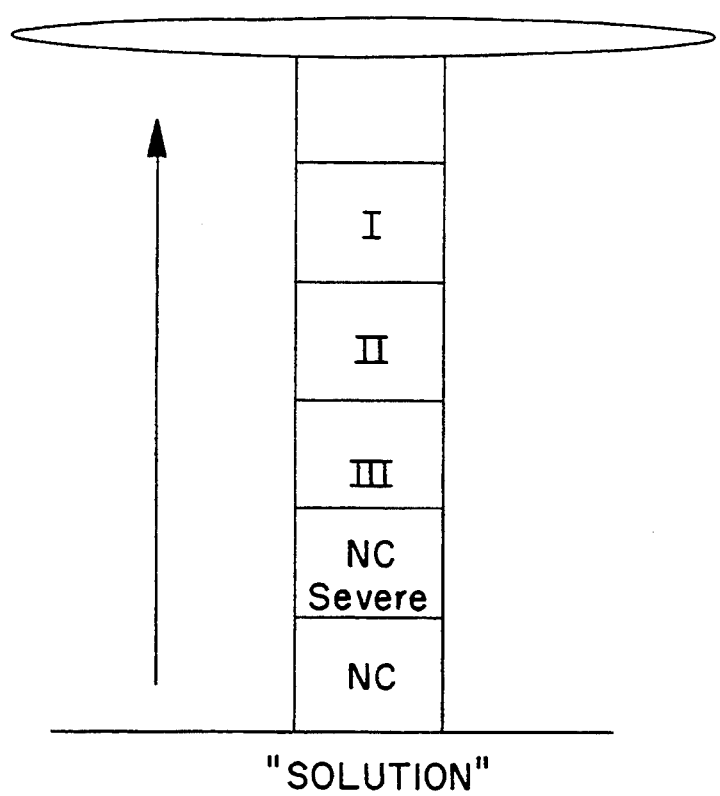
FIG. 9 illustrates a dip stick coated with test microspheres.
Figure 10:
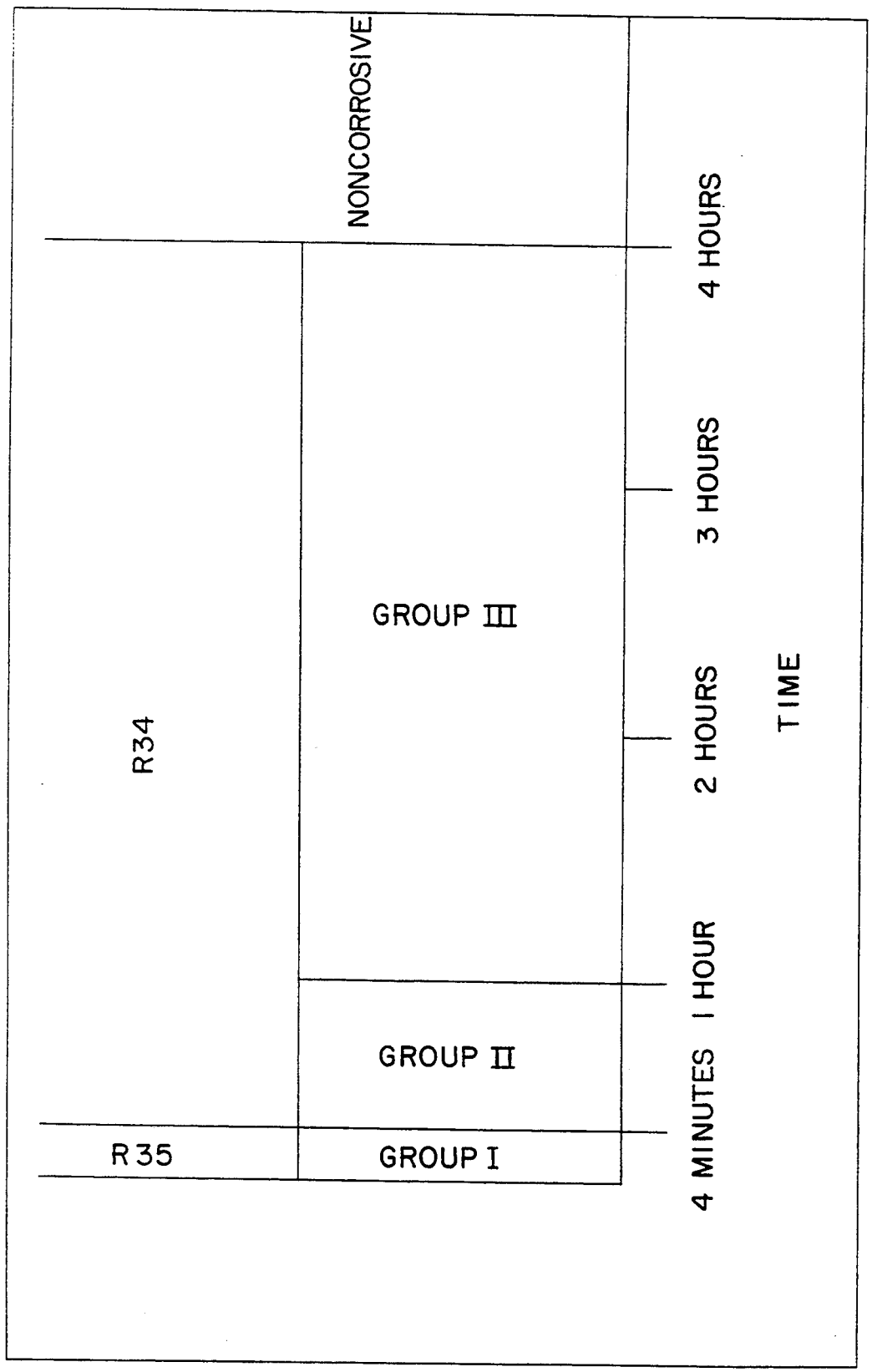
FIG. 10 illustrates a comparison of corrosive substances from three UN Packing Groups and the two EC classes with results of the method of the invention for the same substance.

In another embodiment, shown in FIG. 9, a paper or wooden dipstick can be coated with microspheres having at least one standard thickness of biobarrier of a particular color. When the dipstick is exposed to a corrosive test substance, the biobarrier erodes off the microspheres revealing an underlying particle of other color(s), fluorescence, etc.

In an alternate method, the dipstick can be coated with alternating layers of corrosion-resistant materials and dyes. Thus, highly corrosive substances corrode off more layers and expose an underlying color denoting highly corrosive substances. The corrosion-resistant layers also can incorporate the various dyes.

B.8. The Method

A major virtue of the method of this invention is its simplicity. The crux of the procedure is the application of the substance to be tested to a synthetic or natural biobarrier and exposure of the biobarrier to a chemical detection system which is sensitive to many chemicals. The time to produce a change in the CDS can be read quantitatively by direct measurement or qualitatively by eye.

B.9. Evaluation of the Results

As set forth above, it is desirable to have a direct correlation between the results of the test as performed by the method of the invention and the capacity of a substance to corrode the human skin. However, results of human experience for a large number of corrosives for which testing is desired is not available. Therefore, a threshold criterion for predictive validity of the testing procedures of the invention is correlation of its results with those of in vivo dermal corrosivity testing of the same substances.

Accordingly, the time curves shown in FIG. 10 have been prepared to show the relationship between the detection time obtained using the biobarrier/CDS of the present invention. The tables state the concordance between the inventive method and prior test methods. Concordance of "1" is reported when there is perfect agreement in the classification of corrosivity. When the inventive method and the prior test method disagree by one classification level or more, concordance of "0" is reported.

C. Examples

The invention has been disclosed by direct description. The following are examples showing the efficacy of the method on many chemicals. The examples are only examples and should not be taken in any way as limiting to the scope of the method or device.

C.1. Protocol for Preparing the Biobarrier

To make a Biobarrier:

First, mix the following:

10.0 g Porcine Dermagelatin 300 bloom
(Sigma Chemical Co., St. Louis, Mo.)
0.9 g Sodium Chloride (NaCl)
50.0 ml Deionized $H_2O$ Second, heat to 66° or until the gelatin is dissolved. Use a thermometer to be certain that the temperature does not exceed approximately 70° C.

After the biobarrier protein solution reaches the appropriate temperature and becomes clear, add 50 ml of ethylene glycol. When the ethylene glycol is thoroughly mixed, remove the mixture from the heat.

Immediately begin skimming the air bubbles and foam off the top of the gelatin with a spoon.

The gelatin is now ready to be pipetted onto cellulose base membrane discs in the bottom of wells that measure 3 cm in height and 1 cm in diameter. Add 200 μl per disc base membrane. Working time is approximately 30 minutes.

The biobarrier wells are packaged airtight and stored at 4° C. until ready to use.

Note: The procedure must be carefully followed to ensure consistent assay results. In particular, do not boil the gelatin, or it will "skin-up" upon cooling. If it skins up, do not use it. As much as 80 ml of ethylene glycol may be used; however, the biobarrier will need to be retested for whether it still reflects the corrosivity of human skin. Watch for air bubbles when injecting the gel into the discs.

C.2. Protocol for Chemical Detection System: Preparation of indicator:

Indicator 1. Methyl Orange:

1) Add 50.0 mg of methyl orange solid reagent to 50.0 ml deionized water in a tapered cell culture centrifuge tube.
2) Shake well. This is a 0.1% solution.

Indicator 2. Cresol Red:

1) Add 50.0 mg of cresol red to 50.0 ml of deionized water.
2) Shake solution well. Some greenish particles usually remain. To remove the particles, pour the solution onto analytical grade filter paper in a funnel, and transfer the filtered solution to another test tube.

Chemical Detection System Preparation:

1) To 100.0 ml deionized water, add 1 ml of 0.1% methyl orange and 2.0 ml of 0.1% cresol red solutions. The final concentrations should be 0.001% methyl orange and 0.002% cresol red. Alternately, the same volumes of each indicator solution may be used.
2) Shake well. Label bottle with date, contents (CDS solution) and initials.

C.2. Results

Into each vial, 22 ml of the CDS solution was placed so that it was in contact with the lower surface of the biobarrier/base membrane. Then 500 μl or 500 mg of the test substance was applied to the upper surface of the biobarrier. The time at which the test substance was applied was recorded. The test system was visually observed for a change in color, upon which a second time was recorded. The two times were subtracted, and the detection time was recorded. Over 300 chemicals and formulations have been analyzed to date. Corrosive classifications were assigned based on Table I. In vivo classifications were obtained from industrial laboratories or the Federal Hazardous Material Table (Imokawa, *Cont. Derm.* 5: 357, 1978).

TABLE I

| In Vitro Results | | |
|---|---|---|
| Time (min) | Abbreviation | Classification |
| 0–3 | I | Corrosive Packing Group I |
| 3–60 | II | Corrosive Packing Group II |
| 60–240 | III | Corrosive Packing Group III |
| >240 | NC | Noncorrosive |

Tables II–V list the results of the inventive method for the various chemicals, their in vivo classification as listed in Imokawa (*Cont. Derm.* 5: 357, 1978) or supplied by chemical manufacturers. As indicated, some of the test results were repeated and are shown either on the line below the earlier test results or in parenthesis after the earlier test results. When in vivo tests were repeated, the tests were performed according to the D.O.T. protocol (49 C.F.R. § 173,136).

TABLE II

Test Packing Group I

| Chemical | Conc. | CORROSITEX Results | | | In Vivo DOT Results | Concordance |
|---|---|---|---|---|---|---|
| | | pH of 10% | Time (h:m:s) | Class | | |
| Nitric Acid | 90% | 0 | 0:00:34 | I | I | 1 |
| Selenic Acid | 95% | 0 | 0:01:41 | I | I | 1 |
| Fluorosulfonic Acid | Pure | 0 | 0:00:13 | I | I | 1 |
| Trifluoroacetic Acid | 99% | 0.75 | 0:05:25 | II | I | 0 |

TABLE III

Test Packing Group II

| Chemical | Conc. | CORROSITEX Results | | | In Vivo DOT Results | Concordance |
|---|---|---|---|---|---|---|
| | | pH of 10% | Time (h:m:s) | Class | | |
| Dimethylcyclo-hexyl-amine (2d test) | 90+% | 11.70 | 0:35:00 | II | II | 1 |
| | | | 1:05:00 | III | II | 0 |
| Dichloroacetic acid | 99+% | 0.64 | 0:08:00 | II | II | 1 |
| Dichloroacetyl chloride | 99+% | 0.46 | 0:05:00 | II | II | 1 |
| Chloroacetic acid | 99+% | 1.44 | 0:08:30 | II | II | 1 |
| Bromoacetic acid | 99+% | 1.41 | 0:09:30 | II | II | 1 |
| Cyclohexylamine | 99% | 12.34 | 0:47:00 | II | II | 1 |
| NaOH, solid | pellets | 13.81 | 0:12:00 | II | II | 1 |
| Ethylenediamine | neat | 12.13 | 0:13:00 | II | II | 1 |
| Lithium hydroxide, monohydrate | 98% | 11.8 | 0:20:00 | II | II | 1 |
| Potassium hydrogen sulfate | 35–37% | 0.85 | 0:21:00 | II | II | 1 |
| Ammonium hydrogen sulfate | neat | 0.78 | 0:13:00 | II | II | 0 |
| Glacial acetic acid | 99+% | 2.3 | 0:35:00 | II | II | 1 |
| Aluminum chloride | pure | 2.92 | 0:16:30 | II | II | 1 |
| Acetic anhydride | pure | 1.99 | 0:47:00 | II | II | 1 |
| Trichloroacetic acid | 99+% | 0.74 | 0:11:00 | II | II | 1 |
| Antimony tribromide | 99% | 0.35 | 0:22:00 | II | II | 1 |
| Hydrobenzene sulfonic acid | 65+% | 0.55 | 0:13:00 | II | II | 1 |
| Sulfuric acid | 99.99% | 0 | 0:01:30 | I | II(I) | 0 |
| sulfurous acid | neat | 1.78 | 0:18:00 | II | II | 1 |
| Dimethylcarbamyl chloride | 98% | 2.31 | 0:17:00 | II | II | 1 |
| Boron trifluoride-acetic acid complex | 98% (in vitro repeat) | 0.95 | 0:03:00 0:03:34 | I II | II | 0 1 |
| Ortho-anisoyl chloride | 97% | 0.72 | 0:10:20 | II | II | 1 |
| Diethylene triamine | 99% | 12.01 | 0:34:00 | II | II | 1 |
| Dodecyl trichloro-silane | 98% | 0.5 | 0:11:35 | II | II | 1 |
| Fluoboric acid | 48+% | 1.3 | 0:02:45 | I | II(III) | 0 |
| Valeryl chloride | 98% | 0.45 | 0:10:40 | II | II | 1 |
| Tetramethyl-ammonium hydroxide pentahydrate | 99% | 13.61 | 0:11:30 | II | II | 1 |
| Formic acid | 96% | 1.55 | 0:06:30 | II | II | 1 |
| Hydrogen bromide | 48% | 0.3 | 0:02:47 | I | II | 0 |
| Thiophorphoryl chloride | 98% | 5.81 | 0:10:08 | II | II | 1 |
| Phenyl trichlorosi-lane | 98% | 0 | 0:07:00 | II | II | 1 |
| Antimony trichloride | 99.99% | 0.3 | 0:04:15 | II | II | 1 |
| Mercaptoacetic acid | 97% | 0.3 | 0:11:37 | II | II | 1 |
| Acrylic acid | 99% | | 0:29:00 | II | II | 1 |
| Dichlorophenyl-phosphine | 97% | | 0:02:00 | I | II | 0 |
| Phosphoric acid | 85% | 0.85 | 0:15:00 | II | III(II) | 1 |
| Propionic acid | 99+% | 2.68 | 0:41:00 | II | III(II) | 1 |
| Ferric chloride (repeat) | 98% | 3.00 | 0:23:00 0:21:18 | II II | III II | 0 1 |

TABLE III-continued

Test Packing Group II

| Chemical | Conc. | pH of 10% | CORROSITEX Results Time (h:m:s) | Class | In Vivo DOT Results | Concordance |
|---|---|---|---|---|---|---|
| 2,2 amino ethoxyl ethanol (repeat) | 98% | 11.30 | 0:31:00 | II | III | 0 |
| | | | | | II | 1 |

TABLE IV

Test Packing Group III

| Chemical | Conc. | pH of 10% | CORROSITEX Results Time (h:m:s) | Class | In Vivo DOT Results | Concordance |
|---|---|---|---|---|---|---|
| Dicyclohexylamine | 99% | 9.57 | 3:30:00 | III | III | 1 |
| Tetraethylene-pentamine (repeat) | neat | 11.85 | 0:56:20 | II | III | 0 |
| | | | 1:01:00 | III | III | 1 |
| Copper(II) chloride (repeat) | 97% | 2.99 | 0:42:00 | II | III | 0 |
| | | | 0:42:41 | | | |
| Ethylhexylamine | 98% | 11.98 | 2:45:00 | III | III | 1 |
| Benzene sulfonyl chloride | neat | 1.80 | 3:30:00 | III | III | 1 |
| Hydroxylamine sulfate | 97+% | 3.58 | 3:30:00 | III | III | 1 |
| Crotonic acid | 99+% | 2.30 | 1:22:25 | III | III | 1 |
| Butyric anhydride | 99.2% | 3.08 | 2:30:00 | III | III | 1 |
| Hexanoic acid | 99.5% | 3.00 | 2:29:00 | III | III | 1 |
| Pyridine | 100 | 9.2 | 2:09:40 | III | Not grouped | 1 |

TABLE V

CORROSITEX Noncorrosives

| Chemical | Conc. | pH of 10% | CORROSITEX Results Time (h:m:s) | Class | In Vivo DOT Results | Concordance |
|---|---|---|---|---|---|---|
| Acid dithiodipropionique | 100 | | >4 | NC | NC | 1 |
| Acrylate methoxy ethyl | 100 | | >4 | NC | NC | 1 |
| Benzyl toluene | 100 | | >4 | NC | NC | 1 |
| 1813 | 100 | 10.2 | >4 | NC | NC | 1 |
| SK 602 | 100 | 9.8 | >4 | NC | NC | 1 |
| 1807 | 100 | 10.3 | >4 | NC | NC | 1 |
| 2615 | 100 | 10.0 | >4 | NC | NC | 1 |
| Butoxyethylacetate | 100 | 3.9 | >4 | NC | NC | 1 |
| 2619 | 100 | 10.0 | >4 | NC | NC | 1 |
| 1816 | 100 | 9.9 | >4 | NC | NC | 1 |

In Table VI the DOT in vivo classifications are compared to the classifications obtained by the inventive method and another in vitro classification based on pH and acid alkali reserve (Oliver et al., *Toxic. in Vitro.* 2:7, 1988). The inventive method seems to more accurately assign substances with primarily acid/alkali effects than does a physical chemistry system based on pH determination and analysis of acid alkali reserve. Three substances were underestimated based on assignments using pH and acid/alkali reserve.

TABLE VI

Comparison of CORROSITEX, In Vitro Results, and Predictions Based on pH and Acid/Alkali Reserve

| Chemical | CORROSITEX Grouping | pH | DOT Group | Time (h:m:s) | Assignment Based on pH and Acid/Alkali (24) |
|---|---|---|---|---|---|
| HoAc 25% | II | 1.9 | II | 00:31:28 | C |
| HoAc 10% | II | 2.3 | II | 00:40:10 | NC |
| NaOH 5% | II | 13.7 | II | 00:21:20 | C |
| NaOH 1% | II | 13.3 | II | 00:33:04 | NC |
| KOH 5% | II | 13.9 | II | 00:18:51 | C |
| KOH 1% | II | 13.1 | II | 00:41:21 | NC |
| HCl 1 N | II | 0.4 | II | 00:12:30 | C |

C.3. Results of Anti-Corrosive Study

In one protocol, 500 µl or 500 mg of a test sample was applied to the biobarrier described above. The time to produce a change in the CDS was recorded. The results were categorized according to Table VII.

A second experiment was conducted as discussed above to determine the amount of anti-corrosive necessary to reduce the corrosivity of a test sample. The results are reported in Table VII.

TABLE VII

| Anti-Corrosive Test Results | | |
| --- | --- | --- |
| | Time | Class |
| Corrosive | 00:02:37 | I |
| Anti-Corrosive | >4 h | NC |
| 50/50 Corrosive/ Anti-Corrosive | 00:15:41 | II |

In summary, the invention provides a convenient, inexpensive screening procedure to obtain preliminary data with respect to dermal corrosion potential of a substance. Results obtained were comparable to those obtained from the procedures involving whole animals.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

We claim:

1. A method for determining the degree of corrosive toxicity of a test substance to human skin or membrane which method comprises the steps of
   (a) applying the test substance to a test stick, the stick having been prepared by applying a series of layers to an uncoated test stick said series comprising
   a first layer comprising a material which is weakly resistant to corrosive materials;
   a second layer immediately under the first layer comprising a first dye;
   a third layer underlying the second layer and comprising a more corrosive-resistant material than the first layer;
   a fourth layer immediately under the third layer comprising a second dye;
   a fifth layer underlying the fourth layer comprising the most corrosive resistant substance of the three corrosive-resistant layers;
   a sixth layer, immediately under the fifth layer comprising a third dye; and wherein said first, third, and fifth layers are made from a proteinaceous material mimicking human skin or membrane;
   (b) leaving the test substance in contact with the test stick for more than 1 second;
   (c) observing the color of the test stick where the test substance was applied; and
   (d) correlating the color of the test stick with the degree of corrosivity of the test substance.

2. The method of claim 1, wherein the test substance is removed from the test stick before the color of the test stick is observed.

3. A method for determining the degree of corrosive toxicity of a test substance to human skin or membrane, which method comprises the steps of
   (a) applying the test substance to test microspheres, the microspheres having been prepared by applying a series of layers to particles, said series comprising
   a first layer comprising a material which is weakly resistant to corrosive materials;
   a second layer immediately under the first layer comprising a first dye;
   a third layer underlying the second layer and comprising a more corrosive-resistant material than the first layer;
   a fourth layer immediately under the third layer comprising a second dye;
   a fifth layer underlying the fourth layer comprising the most corrosive resistant substance of the three corrosive-resistant layers;
   a sixth layer, immediately under the fifth layer comprising a third dye; and wherein said first, third, and fifth layers are made from a proteinaceous material mimicking human skin or membrane;
   (b) letting the test substance contact the microspheres for more than 1 second; and
   (c) observing the color of the microspheres.

4. The method of claim 3, wherein the test substance is removed from the microspheres before the color of the microspheres is observed.

5. Microspheres useful for determining the degree of corrosive toxicity of a test substance to human skin or membrane wherein said microspheres are prepared by applying a series of layers to a particle said series comprising
   a first layer comprising a material which is weakly resistant to corrosive materials;
   a second layer immediately under the first layer comprising a first dye;
   a third layer underlying the second layer and comprising a more corrosive-resistant material than the first layer;
   a fourth layer immediately under the third layer comprising a second dye;
   a fifth layer underlying the fourth layer comprising the most corrosive resistant substance of the three corrosive-resistant layers;
   a sixth layer, immediately under the fifth layer comprising a third dye; and wherein said first, third, and fifth layers are made from a proteinaceous material mimicking human skin or membrane.

6. A test stick useful for determining the degree of corrosive toxicity of a test substance to human skin or membrane which test stick is prepared by applying a series of layers to an uncoated test stick, said series comprising
   a first layer comprising a material which is weakly resistant to corrosive materials;
   a second layer immediately under the first layer comprising a first dye;
   a third layer underlying the second layer and comprising a more corrosive-resistant material than the first layer;
   a fourth layer immediately under the third layer comprising a second dye;
   a fifth layer underlying the fourth layer comprising the most corrosive resistant substance of the three corrosive-resistant layers;
   a sixth layer, immediately under the fifth layer comprising a third dye; and wherein said first, third, and fifth layers are made from a proteinaceous material mimicking human skin or membrane.

* * * * *